(12) United States Patent
Veglio et al.

(10) Patent No.: US 6,627,791 B1
(45) Date of Patent: Sep. 30, 2003

(54) RESILIENT, THREE DIMENSIONAL POLYMERIC FILM COMPRISING OPEN AND CLOSED CAPILLARIES, AND ABSORBENT ARTICLE WITH IMPROVED BACKSHEET COMPRISING THE FILM

(75) Inventors: Paolo Veglio, Pescara (IT); Luigi Marinelli, Pescara (IT); Amedeo Franco D'Incecco, Pescara (IT); Giovanni Carlucci, Chieti (IT); Carmine Cimini, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/914,857
(22) PCT Filed: Mar. 31, 2000
(86) PCT No.: PCT/US00/08811
§ 371 (c)(1), (2), (4) Date: Sep. 4, 2001
(87) PCT Pub. No.: WO00/59435
PCT Pub. Date: Oct. 12, 2000

(30) Foreign Application Priority Data

Apr. 1, 1999 (EP) ............................................. 99105195
Apr. 1, 1999 (EP) ............................................. 99105196

(51) Int. Cl.$^7$ ............................. A61F 13/15; B32B 3/10
(52) U.S. Cl. ................... 604/383; 604/385.01; 428/132
(58) Field of Search ........................... 604/383, 385.01; 428/131–133

(56) References Cited

U.S. PATENT DOCUMENTS

| | | | |
|---|---|---|---|
| 3,881,489 A | 5/1975 | Hartwell | |
| 3,989,867 A | 11/1976 | Sisson | |
| 4,306,559 A | * 12/1981 | Nishizawa et al. | ......... 604/371 |
| 4,681,793 A | * 7/1987 | Linman et al. | ............. 428/138 |
| 4,772,444 A | 9/1988 | Curro et al. | |
| 5,591,510 A | 1/1997 | Junker et al. | |
| 6,232,521 B1 | * 5/2001 | Bewick-Sonntag et al. | . 604/378 |
| 6,413,247 B1 | * 7/2002 | Carlucci et al. | ....... 604/385.01 |
| 6,436,080 B1 | * 8/2002 | Carlucci et al. | ....... 604/385.01 |

FOREIGN PATENT DOCUMENTS

| | | | |
|---|---|---|---|
| EP | 0 052 403 A1 | 5/1982 | |
| EP | 0 598 970 A1 | 6/1994 | |
| EP | 0 710 471 A1 | 5/1996 | |
| GB | 2 182 685 | * 11/1986 | ............ D04H/3/00 |
| WO | WO 97/26850 A1 | 7/1997 | |

* cited by examiner

Primary Examiner—Weilun Lo
Assistant Examiner—Jamisue A Webb
(74) Attorney, Agent, or Firm—Kevin C. Johnson; Michael B. Kolodesh (57) ABSTRACT

A resilient, three dimensional, perforated plastic webs which allow passage of water vapor and preferably air, and are resistant to the transmission of aqueous fluids at least in one direction. According to the present invention the perforated plastic webs consist of a liquid impervious polymeric film having open and closed capillaries. More than half of the capillaries are closed and preferably shorter than the capillaries with aperatures, and provide the resilient three dimensional web with an increased resistance crush and to collapse the capillaries under compression. The resilient, three dimensional, perforated plastic webs can be used as one of the layers of a backsheet in an absorbent articles, such as, sanitary napkins, pantiliners. baby diapers, adult incontinence, and the like.

11 Claims, 5 Drawing Sheets

RESILIENT, THREE DIMENSIONAL POLYMERIC FILM COMPRISING OPEN AND CLOSED CAPILLARIES, AND ABSORBENT ARTICLE WITH IMPROVED BACKSHEET COMPRISING THE FILM

FIELD OF THE INVENTION

The present invention relates to resilient, three dimensional, perforated plastic webs which are breathable, but are resistant to the transmission of aqueous fluids at least in one direction. According to the present invention the perforated plastic webs consist of a liquid impervious polymeric film having capillaries extending from one surface of the layer, and comprising a first end with an aperture in the opposite surface of the layer, and a second end. From 5% to 50% of these capillaries comprise a second aperture in the second end, wherein they are also preferably higher than the capillaries without the second aperture. The present invention also relates to absorbent articles like baby diapers, adult incontinence articles and in particular to sanitary napkins or pantiliners provided with a backsheet comprising said webs, preferably to provide breathability.

BACKGROUND OF THE INVENTION

The primary consumer needs which underlie development in the absorbent article field, in particular sanitary napkins, catamenials, or pantiliners is the provision of products providing both a high protection and comfort level.

One means for providing consumer comfort benefits in absorbent articles is by the provision of breathable products. Breathability has typically concentrated on the incorporation of so called 'breathable backsheets' in the absorbent articles. Commonly utilised breathable backsheets are microporous films and apertured formed films having directional fluid transfer as disclosed in for example U.S. Pat. No. 4,591,523. Both these types of breathable backsheets are vapour permeable allowing gaseous exchange with the environment. This thereby allows for the evaporation of a portion of the fluid stored in the core and increases the circulation of air within the absorbent article. The latter is particularly beneficial as it reduces the sticky and soiled feeling experienced by wearers of or associated with articles comprising an apertured formed film or film like topsheet.

The use of apertured film topsheets has long been recognized as providing particular benefits in controlling the liquid flow through this layer into an absorbent structure and reducing the liquid flow out of the absorbent structure towards the skin of a wearer. In this respect apertured film topsheets have provided an exceptional dryness comfort to the wearers of absorbent articles, particularly sanitary napkins. This comfort benefit, however, started to wear off under stress conditions of such articles, such as physical exercising of the wearer (which also caused transpiration from the skin opposite the article to emanate more strongly), heavy loading of the article or extended wearing duration.

A drawback associated with the use of breathable backsheets in absorbent articles is the negative effect on the protection level performance by leakage, known as wet through, onto the users garment. Although, breathable backsheets in principle only allow the transfer of materials in the gaseous state, physical mechanisms such as extrusion, diffusion and capillary action may still occur and result in the transfer of the fluids from the absorbent core through the backsheet and onto the user's garments. In particular, these mechanisms become more dominant if the product is utilised during physical exertion, or for heavy discharge loads or over extended periods of time. Thus, whilst the incorporation of breathable backsheets in absorbent articles is highly desirable from a comfort standpoint, since the primary role of a backsheet still remains the prevention of liquid leakage, conventional breathable backsheets have not been successfully incorporated into products.

The problem of wet through onto users garments due to the incorporation of such breathable backsheets in absorbent articles has indeed also been recognized in the art. Attempts to solve the problem have mainly resided in the use of multiple layer backsheets such as those illustrated in U.S. Pat. No. 4,341,216. Similarly European patent application no. 710471 discloses a breathable backsheet comprising an outer layer of a gas permeable, hydrophobic, polymeric fibrous fabric and an inner layer comprising an apertured formed film having directional fluid transport. The backsheet construction preferably has no liquid transport/wet through under certain specified test conditions. Also European patent application no. 710472 discloses a breathable backsheet consisting of at least two breathable layers which are unattached to one another over the core area. The backsheet construction preferably has no liquid transport/wet through under certain specified test conditions.

U.S. Pat. No. 4,713,068 discloses a breathable clothlike barrier for use as an outer cover for absorbent articles. The barrier comprises at least 2 layers, a first layer having a specified basis weight, fiber diameter and pore size and a second layer comprising a continuous film of poly (vinyl alcohol) having a specified thickness. The barrier also has a specified water vapour transmission rate and level of impermeability.

However, these proposed solutions have not been able to provide a fully satisfactory solution to the problem of breathable backsheet wet through under stress conditions. But especially under such stress conditions breathability would have most pronounced comfort benefits especially for articles comprising film topsheets. For such articles the experienced or assumed stickiness, stuffiness, or soil residue between film and skin is greatest under stress conditions.

U.S. Pat. No. 5,591,510 as well as WO 97/03818 and WO 97/103795 disclose an apertured film layer having capillaries which are disposed at an angle relative to the plain of the film, which films are referred to as slanted capillary films. This film structure is provided as an improvement for incorporation into clothing and garments which are breathable, yet non transmitting liquids toward the wearer of such garments. Also the use of such slanted capillary films is indicated in the context of absorbent articles but as a topsheet, particularly in FIG. 16 of U.S. Pat. No. 5,591,510 the combination of such slanted capillary films together with an absorbent material is disclosed, however not in the context of disposable absorbent articles according to the present invention.

In European patent applications Nos. 98101867.4 and 98101868.2, respectively entitled "Absorbent article with breathable dual layer backsheet comprising one layer with slanted capillary apertures", and "Absorbent article with breathable backsheet comprising slanted capillary apertures and an apertured film topsheet", disposable absorbent articles are described such as baby diapers, adult incontinence articles and in particular sanitary napkins or panty liners. Typically such articles comprise a liquid pervious topsheet forming the wearer facing surface of the article, an absorbent core and a breathable backsheet forming the garment facing surface of the article. The absorbent core is interposed between the topsheet and the backsheet.

The breathable backsheet is located on the garment facing surface of the absorbent core and comprises at least one backsheet layer. The backsheet comprises a resilient three dimensional web, which consists of a liquid impervious polymeric backsheet film which backsheet film has apertures. The apertures form capillaries which have side walls which extend away from the wearer facing surface of the backsheet film and towards the absorbent core providing the web with three dimensionality. The capillaries have a first opening in the garment facing surface of the backsheet film and a second opening at the end of the capillaries spaced apart from the wearer facing surface of the backsheet film. The capillaries are slanted, i.e., they extend away from the wearer facing surface of the backsheet film at an angle which is less than 90° in respect to the plane of the backsheet film, or, in other embodiments, are curved or bent towards the plane of the backsheet film. Further, in alternative or in addition thereto, the capillaries can have a first and a second portion which are different in direction, form, shape, size or combinations thereof.

Also the second opening of at least some of the capillaries may be provided as slits. Slits are considered to be such forms in which the longest extent of an opening is at least 5 times the length of the smallest length of the opening.

Owing to the directional liquid transport capability of the polymeric backsheet film and to the ability to close under pressure derivable from the angled capillaries the breathable backsheets of the above mentioned European patent applications provide a sanitary article with a good leak through protection while maintaining optimum breathability for improved comfort.

However, the performances of resilient, three dimensional polymeric films having apertures that form capillaries, and preferably slanted capillaries as described above, can still be improved in terms of resistance of the three dimensional structure to crush due to collapse of the capillaries, that could be caused by higher compression forces and stresses exerted on the resilient three dimensional film during the use, for example by particularly severe wearing conditions experienced during the use of preferred absorbent articles comprising said resilient, three dimensional polymeric film in a backsheet structure. This increased resistance is even more desirable when the resilient three dimensional polymeric film comprises capillaries, preferably slanted capillaries, which are particularly slender, i.e. being provided with a higher length as compared to the dimension of the respective first opening in the first, base surface of the polymeric backsheet film, in order to facilitate bending, as descried in the European patent applications filed by the applicant at the same time as the present application, and entitled "Resilient, three dimensional polymeric film comprising capillary apertures" (EP 99105197.0, P&G Case CM2063F), and "Absorbent article with improved backsheet comprising capillary apertures" (EP 99106116.9, P&G Case CM2062F). Increased crush resistance in fact provides such a resilient three dimensional polymeric film with a better ability to close under pressure, combined with a reduced risk of collapse of the structure, and therefore with an increased capability of recovering the initial, undeformed state of the capillaries after release of the applied pressure.

It is therefore an object of the present invention to provide an improved resilient three dimensional polymeric film with apertures that form capillaries, which is provided with an increased resistance to crush and to capillary collapse under compression.

Also, the performances of disposable absorbent articles with preferably breathable backsheets comprising at least a resilient three dimensional polymeric film having apertures that form capillaries, and preferably slanted capillaries as described above, can still be improved in terms of resistance of the three dimensional structure to crush due to collapse of the capillaries, that could be caused by higher compression forces and stresses caused by particularly severe wearing conditions experienced during the use of the absorbent articles comprising said backsheets.

An increased resistance to crush and capillary collapse under pressure for the resilient three dimensional polymeric backsheet film is also desirable in backsheets comprising said film and used in disposable absorbent articles in a context different from breathability, for example in order to take advantage of an improved resiliency of these structures in response to compression forces typically exerted in use perpendicularly to the film surface.

It is therefore a further object of the present invention to provide a disposable absorbent article having a backsheet comprising a resilient three dimensional polymeric film with apertures that form capillaries, which is provided with an increased resistance to crush and to capillary collapse under compression.

It is still a further object of a present invention to provide a preferably breathable disposable absorbent article having improved comfort while maintaining an even better leakage protection, i.e. being exceptionally wet through resistant under the stress and pressure experienced during the use.

SUMMARY OF THE INVENTION

The present invention relates to resilient, three dimensional, perforated plastic webs which consist of a liquid impervious polymeric film having a first surface, a second surface, and capillaries. The capillaries have side walls which extend away from the second surface of the film providing the web with three dimensionality. The capillaries have a first end comprising a first opening in the first surface of the film, and a second end spaced apart from the second surface of the film, each of the capillaries defining a conduit constituted by the first end, the second end, and the side walls.

At least 50% of said capillaries are closed capillaries which are closed at the second end, and at least 5% of the capillaries are open capillaries which comprise a second opening at the second end. The open capillaries also preferably extend away from the second surface of the film further than the closed capillaries.

The present invention also relates to disposable absorbent articles of a layered construction such as baby diapers, adult incontinence articles and in particular sanitary napkins or panty liners, which are preferably also breathable. Also articles such as underarm sweat pads or scholar shirts may benefit from the present invention. Typically such articles are of layered construction with each layer or group of layers having a garment facing surface which is oriented to face in the direction of a garment during use of the article and a wearer facing surface facing in the opposite direction. Typically such articles comprise a liquid pervious topsheet forming the wearer facing surface of the article, an absorbent core and a preferably breathable backsheet forming the garment facing surface of the article. The absorbent core is interposed between the topsheet and the backsheet.

The preferably breathable backsheet is located on the garment facing surface of the absorbent core and comprises at least one backsheet layer. The backsheet comprises a resilient, three dimensional web, consisting of a liquid impervious polymeric backsheet film as described above having a garment facing surface, a wearer facing surface, and capillaries. The capillaries have side walls which extend away from the wearer facing surface of the backsheet film towards the absorbent core, providing the web with three dimensionality.

DETAILED DESCRIPTION OF THE INVENTION

The present invention relates to resilient, three dimensional, perforated plastic webs consisting of a liquid impervious polymeric film with capillaries and having an increased resistance to crush and capillary collapse. More briefly, the webs of the present invention are also identified as resilient, three dimensional, polymeric webs having capillaries. In a preferred embodiment of the present invention, the resilient, three dimensional, perforated plastic webs are comprised in disposable absorbent articles for absorption of body fluids, such as sanitary napkins, panty liners, incontinence products and baby diapers, more preferably in a breathable backsheet structure of such disposable absorbent articles.

The present invention also relates to said disposable absorbent articles for absorption of body fluids, such as sanitary napkins, panty liners, incontinence products sweat pads and baby diapers. Typically such articles comprise the elements of a liquid pervious topsheet, a backsheet and an absorbent core intermediate said topsheet and said backsheet. According to the present invention the topsheet, backsheet and core may be selected from any of the known types of these components provided that they meet the desired comfort and protection performance requirements and conditions noted below and in the appended claims.

The resilient, three dimensional, perforated plastic webs of the present invention can however be comprised in any other type of articles, or also be used as such, as a web providing breathability, i.e. water vapour permeability and preferably air permeability, and directional liquid transport capability, e.g. in agriculture.

For example, resilient, three dimensional, perforated plastic webs according to the present invention and providing resistance to fluid transmission in at least one direction, typically combined with water vapour and preferably air permeability, can take advantage of an increased crush and capillary collapse resistance when comprised in e.g. other articles distinct from disposable absorbent articles, such as for example gowns, face masks, bandages, where breathability and resistance to fluid transmission in at least one direction under particularly stressed conditions are highly desirable. Also articles such as underarm sweat pads or scholar shirts may benefit from the present invention.

Resilient, three dimensional, perforated plastic webs according to the present invention having an increased resistance to crush and capillary collapse under pressure can be also advantageously used in a context different from breathability, for example in order to take advantage of an improved resiliency of these structures in response to compression forces typically exerted in use perpendicularly to the film surface. They can be used for example in a backsheet of a disposable absorbent article which is not breathable, in order to provide resiliency and cushioning effect, particularly due to the increased resistance of the structure of the web of the present invention to crush and to capillary collapse.

The resilient, three dimensional, perforated plastic webs of the present invention will be hereinafter described in preferred embodiments where they are comprised in a preferably breathable backsheet structure of a disposable absorbent article such as a sanitary napkin, but the webs of the present invention can also be comprised in other elements distinct form a backsheet structure, e.g. as a topsheet, in disposable absorbent articles, or also in other types of articles, as explained above. Therefore, in the following description, references to the resilient, three dimensional, perforated plastic webs of the present invention as a polymeric backsheet film only represent an example of a preferred embodiment of the present invention.

Typically such preferred disposable absorbent articles comprise the elements of a liquid pervious topsheet, a backsheet and an absorbent core intermediate said topsheet and said backsheet. According to a preferred embodiment of the present invention the topsheet, backsheet and core may be selected from any of the known types of these components provided that they meet the desired comfort and protection performance requirements and conditions noted below and in the appended claims.

In general, the topsheet—if present—should have such a liquid retention to maintain a dry surface and thereby keep the skin of the wearer dry; the absorbent core needs to provide enough absorbent capacity and allow the flow of vapour and/or air through it and the backsheet should prevent wet through (liquid permeability) to retain the absorbed fluid while also being preferably breathable. Furthermore, the individual elements are joined, preferably using techniques such that the final product has the desired comfort and performance level.

In the following description of the invention the surface facing in the direction of the wearer is called wearer facing surface. In the drawings this direction is indicated by arrow 20. Further the surface facing in the direction of the garment is called garment facing surface and in the drawings this direction is indicated by arrow 21.

The disposable absorbent article is described below with reference to a preferred embodiment of the present invention, wherein the article is also breathable and has a breathable backsheet comprising the resilient three dimensional web of the present invention, which comprises capillaries and has an increased crush resistance. However, the resilient three dimensional polymeric web having capillaries and comprised in a backsheet can also be used in the context of a non breathable absorbent article, e.g. in order to provide an improved resiliency and cushioning effect in response to compression forces typically exerted in use perpendicularly to the web surface, particularly due to the increased resistance of the structure of the polymeric web to crush and to capillary collapse.

Absorbent Article Components

The Topsheet

Figure 1:
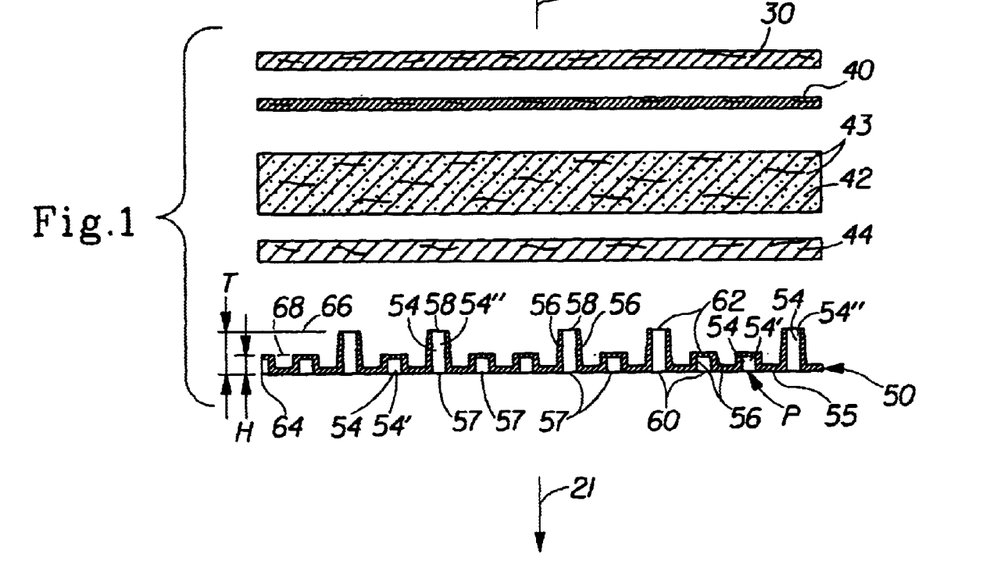
FIG. 1 shows a cross-sectional view of an absorbent article comprising all usual elements of such articles including a resilient, three dimensional, perforated plastic web according to the present invention.

According to a preferred embodiment of the present invention the absorbent article usually comprises a top sheet. In a disposable absorbent article the topsheet generically comprises the topmost layer or layers intended to directly contact the wearer's body. The topsheets suitable for use herein may be any topsheet known in the art. In FIG. 1 the topsheet is indicated with reference numeral 30.

The topsheets for use herein may comprise a single layer or a multiplicity of layers. In a preferred embodiment the topsheet comprises a first layer which provides the user facing surface of the topsheet and a second layer between the first layer and the absorbent structure/core. In addition another layer on the wearer facing surface of the first layer but only extending in the central zone or in parts of the peripheral zone of the article can be desirable to provide extra softness or extra liquid handling/retaining abilities (this design is usually referred to as "hybrid topsheet"). The topsheet typically extends across the whole of the absorbent structure and can extend into and form part of or all of the preferred sideflaps, side wrapping elements or wings. Also the topsheet (or rather at least one layer thereof) can wrap around the absorbent core, thereby providing a topsheet layer and a layer which is considered part of the backsheet.

The topsheet as a whole and hence each layer individually needs to be compliant, soft feeling, and non-irritating to the wearer's skin. It also can have elastic characteristics allowing it to be stretched in one or two directions. As used herein the topsheet hence refers to any layer or combination of layers whose principle function is the acquisition and transport of fluid from the wearer towards the absorbent core and containment of the absorbent core. In addition the topsheet of the present invention should have a high vapour permeability, preferably also a high air permeability.

According to the preferred embodiment of the present invention the topsheet may be formed from any of the materials available for this purpose and known in the art, such as wovens, nonwovens, films or combinations thereof. In a preferred embodiment of the present invention at least one of the layers of the topsheet comprises a liquid permeable apertured polymeric film. One layer, but preferably the wearer facing and contacting layer, is provided by a film material having apertures which are provided to facilitate liquid transport from the wearer facing surface towards the absorbent structure. Such liquid permeable, apertured films are well-known in the art. They provide a resilient three dimensional fiber-like structure. Such films have been disclosed in detail for example in U.S. Pat. No. 3,929,135, U.S. Pat. No. 4,151,240, U.S. Pat. No. 4,319,868, U.S. Pat. No. 4,324,246, U.S. Pat. No. 4,342,314, U.S. Pat. No. 4,591,523, U.S. Pat. No. 4,609,518, U.S. Pat. No. 4,629,643, U.S. Pat. No. 4,695,422 or WO 96/00548.

An example of such film is available from the Procter & Gamble Company, Cincinnati, Ohio, USA under the trade name Dryweave. Also such films are available from the Company Pantex from Pistoia, Italy under the designation "PF-films". Also film according to U.S. Pat. No. 5,591,510 or WO 97/03818 and WO 97/03795 described for use as a layer in breathable backsheets can be employed but may require modification of the apertures to ensure liquid permeability from the wearer facing surface to the absorbent core which is the primary objective of the topsheet and the layers constituting it. Such modification can e.g. be a surface energy alteration which actively drives liquids into and through apertures by creating a gradient of surface tension of the film. A method to provide surface energy gradients is disclosed e.g. in WO 96/00548.

A particularly preferred design would then be to use the same film for the topsheet and the backsheet both possibly supplemented by additional layers. Such a film is e.g. wrapped around and encircles the absorbent core and is treated for liquid transport into the absorbent core in the area corresponding to the topsheet but is not treated in the area corresponding to the longitudinal sides and to the backsheet (or treated to prevent liquid migration from the absorbent core through the backsheet). Treatment in the area corresponding to the topsheet can e.g. provide a discontinuous coating of hydrophobic silicone on the wearer facing surface in line with WO 96/00548. In addition or alternatively the characteristics of the apertures can be made differently (i.e. for liquid transport) in the film area corresponding to the topsheet.

Absorbent Core

According to a preferred embodiment of the present invention the absorbent cores suitable for use herein may be selected from any of the absorbent cores or core system known in the art. As used herein the term absorbent core refers to any material or multiple material layers whose primary function is to absorb, store and distribute fluid. In FIG. 1 the absorbent structure is shown to comprise 3 layers 40, 42, and 44.

The absorbent core of the present invention should have a high vapour permeability preferably also a high air permeability. The absorbent core preferably has a caliper or thickness of less than 12 mm, preferably less than 8 mm, more preferably less than 5 mm, most preferably from 4 mm to 2 mm.

According to the preferred embodiment of the present invention, the absorbent core can include the following components: (a) an optional primary fluid distribution layer preferably together with a secondary optional fluid distribution layer; (b) a fluid storage layer; (c) an optional fibrous ("dusting") layer underlying the storage layer; and (d) other optional components.

Primary/Secondary Fluid Distribution Layer

One optional component of the absorbent core according to the present invention, indicated as layer 40 in FIG. 1, is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilised. The fluid distribution layers can be comprised of any material typical for such distribution layers.

b Fluid Storage Layer

Positioned in fluid communication with, and typically underlying the primary or secondary distribution layers, is a fluid storage layer 42. The fluid storage layer can comprise any usual absorbent material or combinations thereof. It preferably comprises absorbent gelling materials usually referred to as "hydrogel", "superabsorbent", hydrocolloid" materials in combination with suitable carriers, which are indicated as particles 43 in FIG. 1.

The absorbent gelling materials are capable of absorbing large quantities of aqueous body fluids, and are further capable of retaining such absorbed fluids under moderate pressures. The absorbent gelling materials can be dispersed homogeneously or non-homogeneously in a suitable carrier. The suitable carriers, provided they are absorbent as such, can also be used alone.

Suitable absorbent gelling materials for use herein will most often comprise particles of a substantially water-insoluble, slightly cross-linked, partially neutralised, polymeric gelling material. This material forms a hydrogel upon contact with water. Such polymer materials can be prepared from polymerizable, unsaturated, acid-containing monomers which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins and panty liners.

An embodiment of the absorbent structure made according to the present invention comprises a double layer tissue laminate. These layers can be joined to each other for example by adhesive or melting a polymeric powder binder (e.g. PE powder), by mechanical interlocking, or by hydrogen bridge bends. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

if the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

An alternative are foam like or actual foam structures as liquid storage. There are open cell foams which absorb liquid and through chemical or surface interaction retain the liquid also under pressure. Typical foams in this context are e.g. those disclosed in PCT publications WO 93/03699, WO 93/04092, WO 93/04113.

c Optional Fibrous ("Dusting") Layer

An optional component for inclusion in the absorbent core according to the present invention is a fibrous layer adjacent to, and typically underlying the storage layer identified by reference numeral 44 in FIG. 1. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the preferred embodiment of the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

Another component which can be included in the absorbent core according to the invention, and preferably is provided close to or as part of the primary or secondary fluid distribution layer or the fluid storage layer, are odor control agents such as zeolites, carbon black, silicates, EDTA or other chelates. Such agents are preferably provided in particulate form or as part of particles and can be provided together with the absorbent gelling material mentioned supra.

Backsheet

The absorbent article according to the preferred embodiment of the present invention also comprises a backsheet which is preferably also breathable. The backsheet primarily has to prevent the exudates absorbed and contained in the absorbent structure from wetting articles that contact the absorbent product such as underpants, pants, pyjamas, undergarments, and shirts or jackets, thereby acting as a barrier to fluid transport. In addition however, a preferred breathable backsheet of the present invention permits the transfer of at least water vapour, preferably both water vapour and air through it and thus allows the circulation of air into and water vapour out of the article. The backsheet typically extends across the whole of the absorbent structure and can extend into and form part or all of side flaps, side wrapping elements or wings, if present.

According to the preferred embodiment of the present invention suitable preferably breathable backsheets for use herein comprise at least one liquid impervious polymeric backsheet layer. The backsheet comprises a resilient three dimensional web according to the present invention, which consists of a liquid impervious film which has capillary apertures and is air permeable. Preferred breathable backsheets for use herein are those having a high vapour exchange, most preferably both a high vapour and high air exchange. The film with capillaries is oriented such that it retards or prevents liquid from passing from the absorbent core towards the outside while allowing free air flow through it.

According to the preferred embodiment of the present invention any additional backsheet layer needs to provide at least water vapour permeability so as to support breathability of the article. It is not required but desirable that it also supports air permeability in order to further improve the comfort benefit from the breathability of the article. In this context suitable water vapour and air permeable layers include two-dimensional micro- or macro-apertured films, which can also be micro- or macroscopically expanded films, formed apertured films and monolithic films, as well as nonwovens, or wovens. Such films are disclosed in detail e.g. in EP 293482 and the references therein, or U.S. Pat. No. 3,929,135, U.S. Pat. No. 4,637,819 and U.S. Pat. No. 4,591,523.

The resilient, three dimensional, polymeric web according to the preferred embodiment of the present invention provides air and water vapour permeability by being apertured. In a preferred embodiment of the present invention illustrated in FIG. 1 the breathable disposable absorbent article, which can be for example a sanitary napkin or a pantiliner, comprises a backsheet 50 which is also breathable. The breathable backsheet 50 comprises a resilient, three dimensional liquid impervious polymeric backsheet film 55 constituted by the resilient, three dimensional polymeric web of the present invention and having a first surface corresponding in this embodiment to a garment facing surface and a second surface corresponding to a wearer facing surface, both surfaces being planar and parallel to each other, and also parallel to the plane P of the backsheet film 55. In the embodiment of the present invention shown in FIG. 1, the plane P actually corresponds to the garment facing surface of the backsheet film 55.

The terms "planar" and "plane" as used herein refer to the configuration of the backsheet film 55 as such, as if the backsheet film alone were laid on a flat surface, even if the backsheet film 55 may also be not planar when comprised in an e.g. non planar absorbent article according to an alternative embodiment of the present invention.

The backsheet film 55 also comprises capillaries 54 with side walls 56 which extend away from the wearer facing surface of the backsheet film 55 and towards the absorbent core 40, 42, 44. Each capillary 54 has a first end 60 comprising a first opening 57 in the garment facing surface of the backsheet film 55, and a second end 62 spaced apart from the garment facing surface of the backsheet film 55. Each capillary 54 defines a conduit 70 constituted by the first end 60, the second end 62, and the side walls 56.

As shown in FIG. 1, part of the capillaries 54 of the resilient, three dimensional liquid impervious polymeric backsheet film 55 are closed capillaries 54' which are closed at their second end 62, while the remaining part of the capillaries 54 are open capillaries 54" comprising a second opening 58 at their respective second end 62. Moreover, the open capillaries 54" are preferably higher than the closed capillaries 54', i.e. the open capillaries 54" preferably extend from the wearer facing surface of the backsheet film 55, and towards the absorbent core 40, 42, 44, further than the closed capillaries 54'. The closed capillaries 54' constitute from 50% to 95% of the total number of the capillaries 54 of the resilient, three dimensional liquid impervious polymeric backsheet film 55 comprised in the preferably breathable backsheet 50 of the absorbent article according to the present invention. Preferably, the closed capillaries 54' constitute from 50% to 80% of the total number of capillaries 54. The closed capillaries 54' can be preferably evenly distributed among the open capillaries 54" of the resilient, three dimensional liquid impervious polymeric backsheet film 55, or, alternatively, they can be located in well defined areas of the backsheet film 55, for example in one or more stripes, wherein the open capillaries 54' are all grouped in adjacent parallel stripes.

In a preferred embodiment of the present invention such as that illustrated in FIG. 1, the open capillaries 54" in the resilient, three dimensional liquid impervious polymeric backsheet film 55 are all substantially identical, and also the closed capillaries 54' are all substantially identical to one another. Also, open capillaries 54" and closed capillaries 54' of the film 55 illustrated in FIG. 1 have first openings 57 of substantially the same shape and size. Alternatively, open capillaries 54" and closed capillaries 54' of different sizes, and/or having different first openings 57 are also possible. In such a preferred embodiment, the relationship between the respective heights of the open capillaries 54" and of the closed capillaries 54' can be expressed in terms of apparent thickness T of the backsheet film 55, and of height H of the closed capillaries 54', as defined hereinafter.

The resilient, three dimensional liquid impervious polymeric backsheet film 55 has an apparent thickness T that can be defined as the distance measured between a first plane 64 comprising the first ends 60 of the capillaries 54, and actually corresponding to the plane of the garment facing surface of the polymeric backsheet film 55 and therefore to the plane P of the backsheet film 55, and a second plane 66 parallel to the first plane 64 and comprising the points of the second ends 62 which are furthest from the first plane 62. The height H of the closed capillaries 54' can similarly be defined as the distance measured between the first plane 60 and a third plane 68 parallel to both the first plane 64 and the second plane 66, and comprising the points of the second ends 62 of the closed capillaries 54" which are furthest from the first plane 64.

In the embodiment of the present invention illustrated in FIG. 1, where both the open capillaries 54" and the closed capillaries 54' of the backsheet film 55 have the regular shape of respectively identical straight cylinders perpendicular to the first plane 64, with flat and regular second ends 62, which in the open capillaries 54" also comprise respective second openings 58 with smooth edges, the second plane 66 actually entirely comprises the second ends 62 with the respective second openings 58 of the open capillaries 54", while the third plane 68 similarly comprises the flat second ends 62 of the closed capillaries 54'.

According to a preferred embodiment of the present invention, the height H of the closed capillaries 54" is less than 50% of the apparent thickness T of the backsheet film 55, preferably from 30% to 40% of the apparent thickness T.

Figure 6:
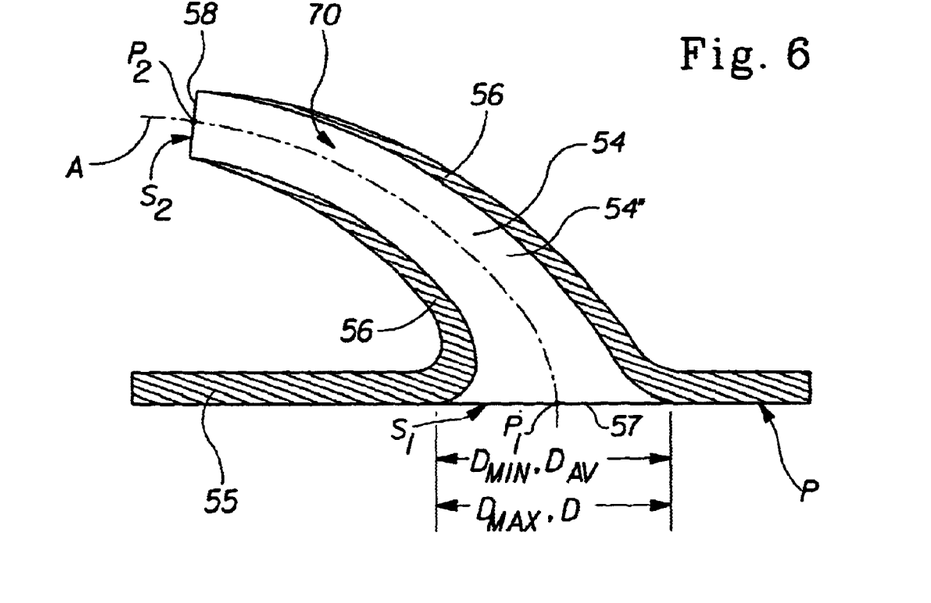
Figure 7:
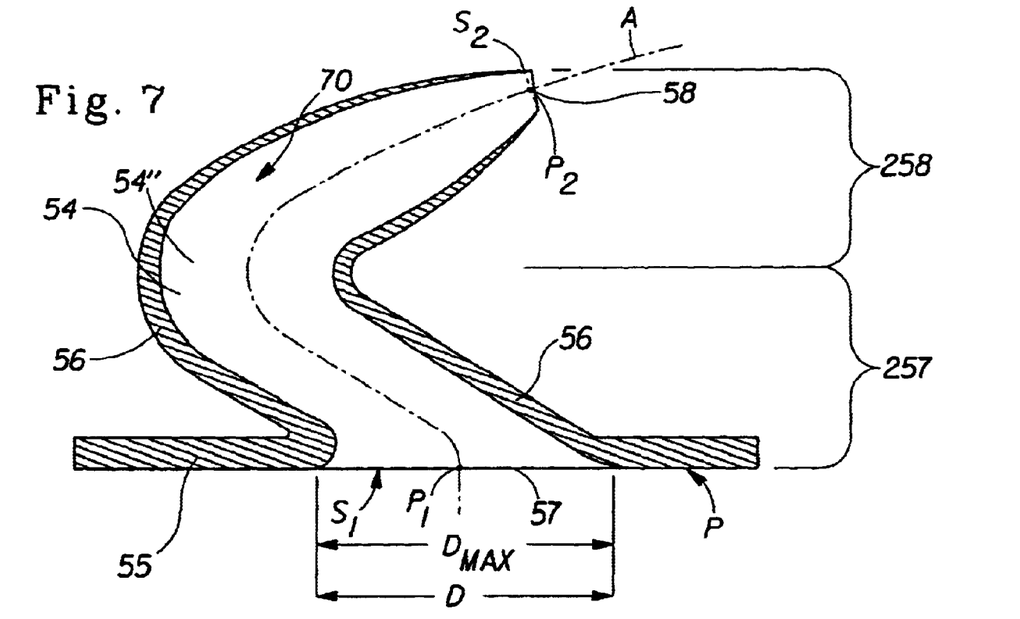
Figure 8:
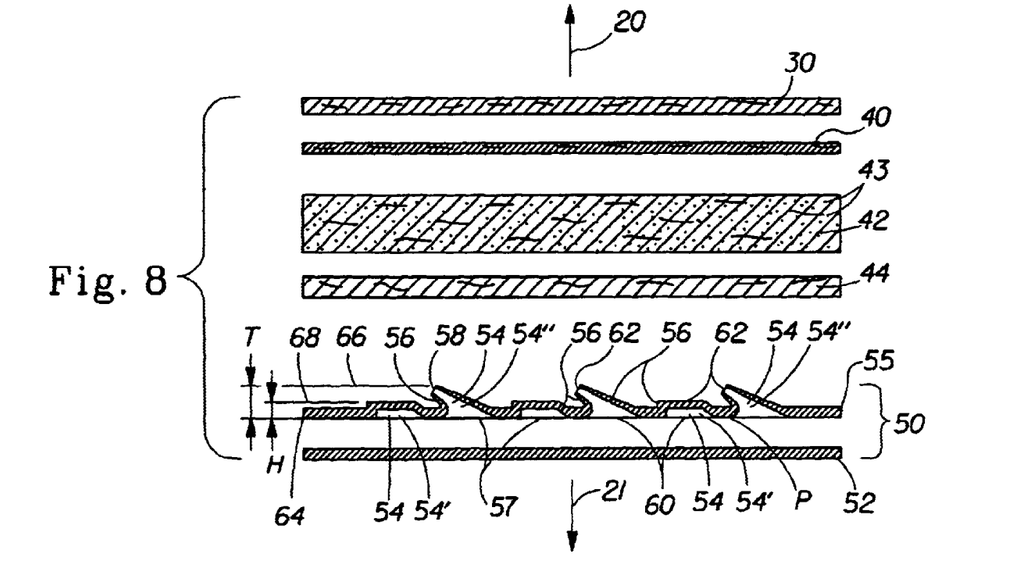
FIG. 8 shows a cross sectional view of an absorbent article similar to that of FIG. 1, with a different embodiment of a resilient, three dimensional, perforated plastic web according to the present invention, comprised in an alternative backsheet structure.

In alternative embodiments of the present invention, where the capillaries 54 in the polymeric backsheet film 55 of the present invention can have different configurations, such as for example the alternative embodiments for the open capillaries 54" of a film 55 of the present invention illustrated in FIGS. 3 to 7, the first, second, and third planes 64, 66, and 68 can be defined according to the description given above and as shown for example in FIG. 8, where a film 55 with capillaries having alternate embodiments and comprised in a backsheet structure of a disposable absorbent article is illustrated, and the respective apparent thickness T and height H accordingly evaluated.

The definition of the different planes 64, 66, and 68 and the measurement of T and H in a film 55 according to the present invention can be obtained with methods known in the art, for example by means of image analysis performed on photomicrographs of the polymeric film 55 taken with a scanning electron microscope.

Necessary adjustments can also be made by the skilled man to perform such measurements in case of less regular structures, for example when the film 55 in a less preferred embodiment of the present invention does not comprise closed and open capillaries 54', 54" that are respectively substantially identical to one another, or, also, when e.g. the open capillaries 54" do not have a smooth edge of their second opening 58, as it is often the case with known actual open capillaries formed in polymeric film structures with known manufacturing methods. In such cases, when the second and third planes as defined herein are not immediately identifiable as described above (the first plane, in contrast, can be always positively identified for a given three dimensional polymeric film), the apparent thickness T of the film 55 can be measured as an average value again by means of image analysis, or alternatively with one of the mechanical thickness measurement devices used in the art for this scope, such as for example the Micrometer TMI Model 49-61 sold by Precision Micrometer Testing Machine Inc. of Amityville, N.Y., USA, with a very low measuring pressure, e.g. 14.7 g/cm$^2$, in order to minimize possible deformation of the three dimensional structure of the capillaries, namely the open capillaries, which are typically more deformable than the closed capillaries, and preferably also higher than them, during the measuring process. The height H can also be evaluated as an average value by image analysis means.

Without being bound to any theory, it is believed that the structure of the closed capillaries 54' is more resistant than that of the higher, open capillaries 54", typically to compressive forces exerted in a direction perpendicular to the plane of the film 55, and also to bending forces applied to the resilient, three dimensional liquid impervious polymeric film 55, which are for example typically encountered during the use of an absorbent article comprising the film 55 in the backsheet 50, according to a preferred embodiment of the present invention. This is due to the closed construction of the closed capillaries 54', and also to the preferred lower height of the closed capillaries 54' that makes them less prone to bend or crush or in any case to deform under stress. The thickness of the film layer in the preferred structure of the closed capillaries 54' is also typically thicker than in the structure of the open capillaries 54", since the capillaries are generally obtained by stretching a heated thermoplastic film over a perforated forming screen by means of e.g. a differential pressure. In the preferably shorter closed capillaries 54' the film is stretched to a lesser extent as compared to the open, longer capillaries 54", and therefore the residual thickness of the film will be higher, and consequently also the resistance of the closed capillary structure.

The higher resistance to compression of the closed capillaries 54' of the resilient, three dimensional liquid impervious polymeric film 55 gives the film 55 a better stability under the stresses induced during the use, for example being comprised in a backsheet structure of a disposable absorbent article. The open, longer capillaries 54" can bend or deform under pressure, but collapse is avoided since the closed capillaries 54' create a reinforced structure that prevents the open capillaries from bending or deforming beyond their recovering capability. After release of the stress the open capillaries can therefore substantially recover their original, unstressed state, and this provides an advantage particularly when the resilient, three dimensional liquid impervious polymeric film described so far is preferably comprised in a breathable backsheet structure of a disposable absorbent article, since the capillaries can close under pressure, therefore minimizing the risk of wet through, more likely to occur in the stressed conditions, but at the same time they do not collapse under pressure and therefore they can recover their original structure and regain their full breathability after the stress has been released.

The resilient, three dimensional liquid impervious polymeric film of the present invention described so far and preferably comprised in a backsheet of an absorbent article can advantageously comprise open capillaries 54" having the preferred structure described in European patent applications Nos. Nos. 98101867.4 and 98101868.2. According to the already mentioned applications the capillaries extend away from the wearer facing surface of the backsheet film at an angle which is less than 90° in respect to the plane of the backsheet film, or, in other embodiments, are curved or bent towards the plane of the backsheet film. Even more preferably, the open capillaries 54" comprised in the polymeric film 55 according to the present invention can be made according to the European patent applications filed by the applicant at the same time as the present application, and entitled "Resilient, three dimensional polymeric film comprising capillary apertures" (EP 99105197.0, P&G Case CM2063F) and "Absorbent article with improved backsheet comprising capillary apertures" (EP 99106116.9, P&G Case CM2062F), which have a preferred ratio between their length and the dimension of their first opening 57.

Figure 2:
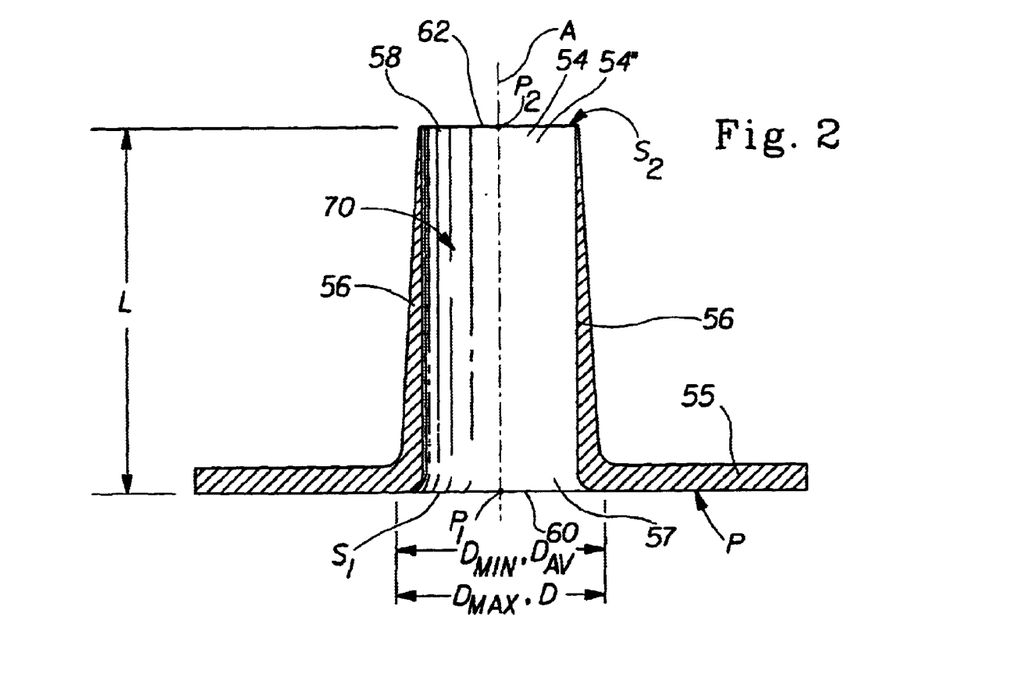
FIG. 2 shows an enlarged cross section of a capillary in a resilient, three dimensional, perforated plastic web according to the present invention.

As better illustrated in FIG. 2, which shows a cross-sectional view of a single capillary corresponding to an open capillary 54" of the polymeric backsheet film 55 of FIG. 1, the open capillaries 54" have side walls 56 which extend away from the wearer facing surface of the polymeric backsheet film 55 towards the absorbent core 40, 42, 44. The open capillaries 54" have a first opening 57 in the plane of the garment facing surface of the polymeric backsheet film 55, and a second opening 58 at the end of the capillaries 54 which is spaced apart from the wearer facing surface of the polymeric backsheet film 55. Each open capillary 54" defines a conduit 70 constituted by the first opening 57, the second opening 58, and the side walls 56. Each capillary 54 also has a centreline A defined as the geometrical axis of the conduit 70. In the embodiment of FIG. 2, where the conduit 70 has a cylindrical shape, the centreline A simply corresponds to the straight line constituting the axis of the cylinder and being perpendicular to the plane P of the backsheet film 55.

In alternative embodiments of the present invention, where the conduit 70 defined by the open capillaries 54" can have different shapes, such as for example those illustrated in FIGS. 3–7, the centreline A is not necessarily a straight line, but can be an at least partially curved line corresponding to the geometrical axis of the conduit, identified as known from solid geometry.

In most preferred embodiments of the present invention as those illustrated in the attached drawings, where the sectional views of FIGS. 2 to 7 are taken from a symmetry plane perpendicular to the plane P of the backsheet film, the identification of the centreline A of the conduit 70 can be more simply done on these same sectional views, since said centreline A entirely lies on this symmetry plane. For example, in the region where the conduit 70 merges the plane P of the backsheet film 55 in FIGS. 3–7 the identification of the centreline A as the geometrical axis of the conduit 70 must take into account the fact that the conduit 70 typically has not a regular shape in this region, as compared to the remaining portion of the open capillary 54" where the conduit 70 is entirely defined as a cylinder or a truncated cone, and where the centreline A is straightforwardly defined. A good approximation to identify the centreline A in this merging region is to connect the points at the centre of some sections of the conduit 70 which are parallel to the plane P, and are taken at different distances from the plane P (which surfaces of course correspond to segments parallel to the plane P in the section views of the drawings). This practical method can be used to draw the centrelines in the conduits 70 illustrated in FIGS. 3 to 7. This is also consistent with the identification of the intersection point between the centreline A and the surface of the first opening 57 in the plane P of the backsheet film 55, as will be explained hereinafter.

The first opening 57 of the open capillary 54" in the garment facing surface of the polymeric backsheet film 55 has a smallest dimension $D_{min}$ and a largest dimension $D_{max}$ respectively defined as the minimum and the maximum open measurements within the area of the first opening 57 in the plane of the garment facing surface of the polymeric backsheet film 55 (plane P), i.e., being measured when said garment facing surface of the polymeric backsheet film 55 is laying on a flat surface. The smallest and the largest dimensions $D_{min}$ and $D_{max}$ can be evaluated with means known in the art, such as for example by image analysis techniques.

An average dimension $D_{av}$ can also be evaluated for the first opening 57, as corresponding to the hydraulic diameter of a conduit having the same cross-section as the first opening 57 in the plane of the garment facing surface of the polymeric backsheet film 55, wherein the whole perimeter of said first opening 57 is wetted by the fluid. Of course the concept of "hydraulic diameter" is used herein by way of definition only, since the conduit 70 of the capillaries 54 is not intended for transport of liquids, and the term "fluid" is therefore used in its broader meaning comprising gaseous fluids, namely air and/or water vapour. As it is well known from hydraulics, the hydraulic diameter of a conduit having a cross-sectional area and a wetted perimeter corresponds to four times the ratio between said cross-sectional area and said wetted perimeter, that in turn corresponds in this context to the entire perimeter of the cross-sectional area of the first opening 57.

In the embodiment illustrated in FIG. 2, where the conduit 70 has the shape of a cylinder having a certain diameter, the first opening 57 in the garment facing surface of the polymeric backsheet film 55 has typically a circular shape with a diameter slightly larger than the diameter of the cylindrical conduit 70, owing to the curvature imparted to the film 55 around the first opening by e.g. the manufacturing method and apparatus used for the formation of the polymeric backsheet film 55.

In this case it is this larger diameter that corresponds to the largest dimension $D_{max}$ of the first opening 57. Of course in the case of FIG. 2, where the first opening 57 has a circular shape, the values of $D_{min}$, $D_{av}$, and $D_{max}$ correspond.

Each open capillary 54" also has a length L measured along the centreline A between the first opening 57 and the second opening 58. The length L is intended to be measured along the centreline A between two points of intersection $P_1$ and $P_2$ defined as follows.

The first point $P_1$ corresponds to the intersection of said centreline A with the surface $S_1$ of the first opening 57. Said surface $S_1$ is flat, as can be seen in the embodiments illustrated in the drawings, and belongs to the plane of the garment facing surface of the polymeric backsheet film 55 (plane P). From a practical point of view, in the embodiments of the present invention such as those illustrated in FIGS. 2 to 7, the first point $P_1$ corresponds to the centre of the first surface $S_1$, as already explained with reference to the identification of the centreline A of the conduit 70 of the open capillaries 54" having different shapes.

The second point $P_2$ corresponds to the intersection between the centreline A of the conduit 70 and a flat surface $S_2$ which is perpendicular to said centreline and passes through the point or points of the perimeter of the second opening 58 which is/are closer to the respective first opening 57 of the open capillary 54", wherein said distance is evaluated along the inner surface of the side wall 56 of the open capillary 54".

Also these measurements can be obtained with methods known in the art, for example by means of image analysis performed on photomicrographs of the polymeric backsheet film 55 taken with a scanning electron microscope.

In the embodiment of FIG. 2, where the open capillary 54" has a regular cylindrical shape, and the second opening 58 also has a regular circular perimeter, the flat surface $S_2$ perpendicular to the centreline A which identifies the intersection point $P_2$ corresponds to a flat circular surface passing through the whole perimeter of the second opening 58. It is generally preferred that said second opening 58 be as smooth as possible so as not to create a liquid transport entanglement between the extending elements at the end of the second opening 58 of the open capillary 54" with the absorbent core 44 in the absorbent article in contrast this may be desirable for use of such a film as an apertured film topsheet where such loose elements provide the function of sucker feet to enhance liquid transport). However, in other cases, and depending on the method used for the formation of the polymeric backsheet film 55, the perimeter and shape of the second aperture 58 may not be regular.

Figure 4:
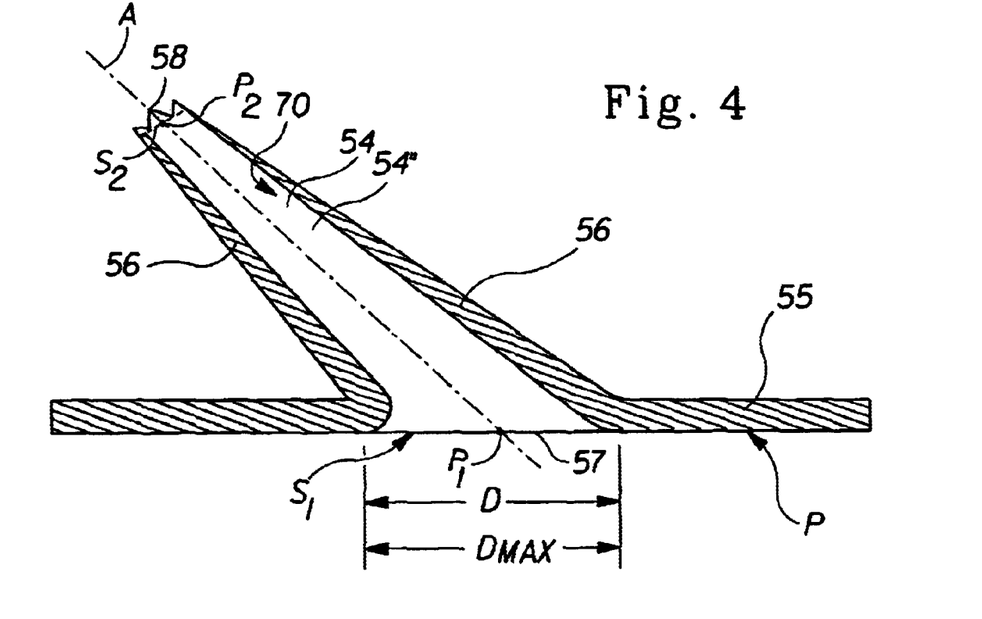

For example, the edge of the second opening 58 may be rugged or uneven, comprising loose elements extending from the edge of the opening, as illustrated in FIG. 4. In this embodiment, the surface $S_1$ of course lies in the plane of the garment facing surface of the polymeric backsheet film 55, such as the corresponding surface $S_1$ of FIG. 2, while the surface S2, defined as explained above with reference to the identification of the second point $P_2$, is indicated as a section in FIG. 4 with a dotted line.

In FIGS. 3 to 7 are shown by way of example the centrelines A and the corresponding features $S_1$, $S_2$, $P_1$, $P_2$, in open capillaries 54" having different and less regular shapes, as compared to the regular shape of a straight cylinder perpendicular to the plane of the polymeric film 55. Usually the centreline A passes through a first point $P_1$ which corresponds to the centre of the surface $S_1$, identified for regular and irregular shapes of the surface $S_1$ as known from plane geometry. In the sectional view of FIG. 6 the dimensions $D_{min}$, $D_{av}$, and $D_{max}$ of the first opening 57 coincide, as it is the case with the open capillary 54" of FIG. 2, since it is considered that the first opening 57 has a circular shape in said figure.

On the contrary, in FIGS. 3–5 and 7 the surface $S_1$ has typically an elliptical shape, with the longer axis shown in the sectional views. In these cases the dimension shown in these figures corresponds to the largest dimension $D_{max}$ as defined herein.

For each open capillary 54" of the polymeric backsheet film 55 comprised in the breathable absorbent article of the present invention a ratio can be defined between the length L of the open capillary 54", and the dimension D of the respective first opening 57, wherein D can correspond to $D_{min}$, $D_{av}$, or $D_{max}$.

According to a particularly preferred embodiment of the present invention, by selecting this ratio it is possible to improve the performances of the resilient, three dimensional, polymeric web according to the present invention, preferably incorporated as the polymeric backsheet film 55 with open capillaries 54" in the breathable backsheet of the disposable absorbent article described so far, in terms of increased breathability combined with a better wet through resistance of the structure of the resilient, three dimensional polymeric web under pressure and stress, e.g. typically exerted by the user on a disposable absorbent article incorporating the resilient, three dimensional polymeric web in a backsheet structure, for example a sanitary napkin or pantiliner, during the wearing time.

Resiliency and cushioning effect in response to compressive forces exerted substantially perpendicularly to the polymeric film surface can also be improved according to the present invention. This effect can be also desirable in the context of a non breathable structure, e.g. a non breathable backsheet.

Accordingly, the ratio between the length L of the open capillaries 54" and the smallest dimension $D_{min}$ of the first opening 57 is preferably greater than 2. More preferably, the ratio between the length L and the average dimension $D_{av}$ of the first aperture 57 should be greater than 2, even more preferably the ratio between the length L and the largest dimension $D_{max}$ of said first aperture 57 should be greater than 2. Most preferably the ratio between the length L and any of $D_{min}$, $D_{av}$, or $D_{ma}$, can be greater than 2.5.

Without wishing to be bound by theory it is believed that the capillaries in the preferred polymeric backsheet film of the preferably breathable backsheet in the disposable absorbent article according to a preferred embodiment of the present invention allow air and water vapour permeability, and at the same time they can easily bend owing to the preferred L/D ratio under the pressure exerted from the wearer facing side on them by the user during the wearing time. The bending causes the capillaries to close under pressure such that liquid transport through them, and towards the outside of the article in the preferred embodiment described so far, becomes nearly impossible. Hence the resilient, three dimensional, polymeric webs of the present invention are highly preferable in the context of breathable absorbent articles. This also gives the resilient, three dimensional polymeric web of the present invention, corresponding to the polymeric backsheet film 55 of the preferred embodiment, a better resilience and the capability of providing a cushioning effect under the pressures in use.

As explained hereinbefore, in case of a capillary having a circular first opening 57, no distinction between $D_{min}$, $D_{av}$, and $D_{max}$ is necessary or possible since the three relevant dimensions D of the first opening 57 correspond to one another.

In case of open capillaries 54" with a first aperture 57 having a shape different from a circle the three relevant dimensions $D_{min}$, $D_{av}$, and $D_{max}$ actually differ from one another. In order to better express the easiness of bending under an external pressure of a capillary having the preferred L/D ratio, one of the three relevant dimensions of the first aperture can be more indicated, depending on the particular shape of said first opening, i.e., whether it is regular or irregular, or having a perimeter which is internally totally concave, such as for example circular, oval, or elliptic, or alternatively partially concave and partially convex. In this latter case, the use of $D_{av}$ or, more preferably, of $D_{max}$ in the ratio L/D are preferred.

As already mentioned, in a particularly preferred embodiment of the present invention illustrated in FIGS. 3 to 8 the open capillaries 54" of the polymeric backsheet film 55 can be also slanted, i.e., disposed at an angle relative to the plane of the polymeric backsheet film which is less than 90 degrees.

Preferably a polymeric backsheet film 55 can be provided with open capillaries 54" in accordance with the aforementioned U.S. Pat. No. 5,591,510 or PCT WO 97/03818, WO 97/03795. In FIGS. 3 through 7 alternative embodiments of such open capillaries are shown. Preferably the open capillaries are evenly distributed across the entire surface of the layer, and are all identical. However, layers having only certain regions of the surface provided with open capillaries, for example only an area outside the region aligned with the central loading zone of the absorbent core, may be provided with open capillaries according to the present invention.

Methods for making such three-dimensional polymeric films with open and closed capillaries are substantially similar to those found in the apertured film topsheet references, the apertured formed film references and the micro/macroscopically expanded film references cited above. Typically a polymeric film such as a polyethylene (LDPE, LLDPE, MDPE, HDPE or laminates thereof) is heated close to its melting point and exposed through a forming screen to a suction force which pulls those areas exposed to the force into the forming apertures which are shaped such that the film is formed into that shape and, when the suction force is high enough, the film breaks at its end thereby forming an aperture through the film corresponding to an open capillary. Closed capillaries are similarly formed by e.g. reducing the suction force with suitable means in correspondence of them, therefore causing the polymeric film to extend only partially without breaking at the second end, and forming the closed capillaries which are also preferably shorter than the open capillaries, as already explained. Other film materials include e.g. polyesters, polyethers, polyvinyl alcohols and others.

Hydrophilic continuous films that are substantially liquid impervious, but moisture vapour permeable per se can also be used for the manufacture of the three dimensional polymeric films with open and closed capillaries according to the present invention. Such films do not allow the flow of moisture vapour through open pores or apertures in the material, but do transfer substantial amounts of moisture vapour through the film by absorbing water on one side of the film where the moisture vapour concentration is higher, and desorbing or evaporating it on the opposite side of the film where the moisture vapour concentration is lower. These films, referred to as monolithic films, are known in the art, such as e.g. Hytrel (TM) film from Du Pont, Corporation, USA.

When a monolithic film is used to manufacture a three dimensional polymeric film with open and closed capillaries according to the present invention, it is capable of maintaining breathability of the polymeric film with capillaries even in areas of the film where, under particularly stressed use conditions, the capillaries are totally closed due to bending, under e.g. high pressure exerted by the user, and also in correspondence of the closed capillaries.

Various forms, shapes, sizes and configurations of the capillaries are possible and will be discussed in reference to FIGS. 3 through 7 in the following.

Figure 5:
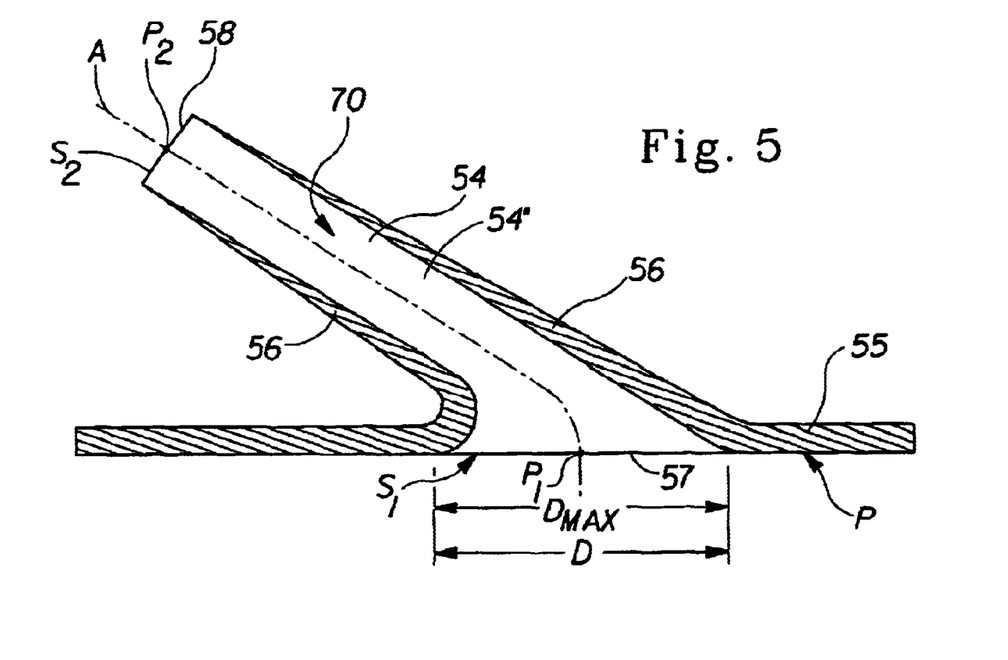

FIG. 5 shows a cross-sectional view of a single slanted open capillary 54" of a preferred polymeric backsheet film 55 made in accordance with U.S. Pat. No. 5,591,510 or PCT WO 97/03818, WO 97/03795, and also having the preferred ratio between the length L and the dimension D of the first opening 57 according to the present invention, wherein elements corresponding to those already described in FIG. 2 are identified by the same numerals. The centreline A forms along at least part of its length an angle of less than 90 degrees with the plane P of the film which is the same plane as the garment facing surface of the film 55. This angle should be preferably in the range between 85 and 20 degrees, more preferably between 65 degrees and 25 degrees, and most preferably between 55 and 30 degrees.

Figure 3:
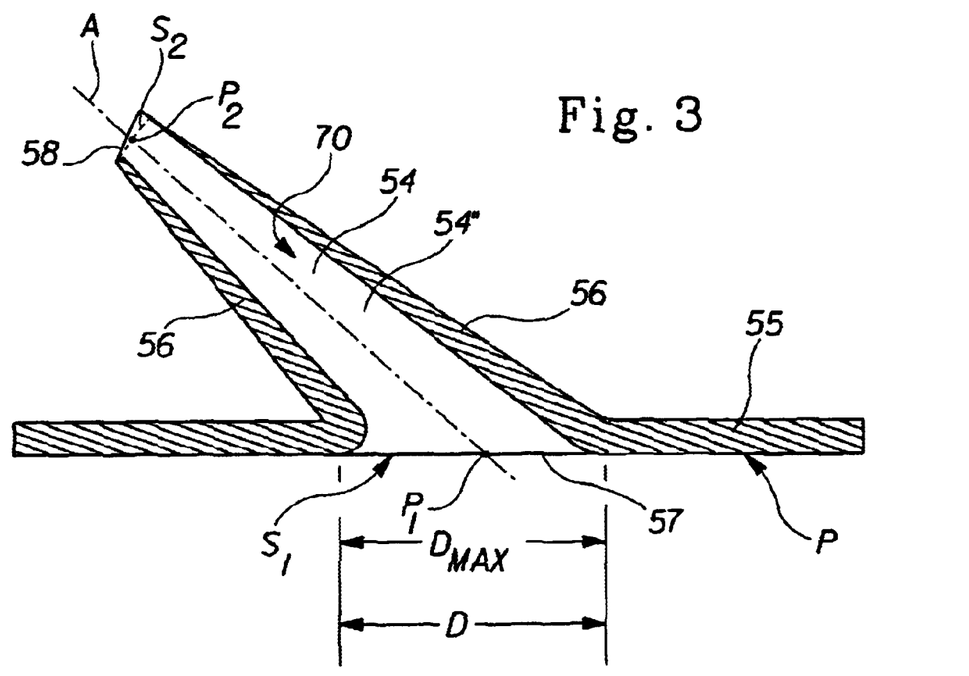
FIGS. 3–7 show particular alternative embodiments of slanted capillaries used for the three dimensional web according to the present invention.

An angle of less than 90 degrees with the plane P can be formed by the centreline A of the open capillary along its entire length when, as illustrated in FIGS. 3 and 4, the centreline A is substantially rectilinear or, as in FIG. 5, where the centreline A is rectilinear along most of its length. This angle can be said to actually corresponds to the angle of the open slanted capillary.

In alternative embodiments where the centreline A of an open capillary 54" is curved entirely or in part, such as for example those illustrated in FIGS. 6 and 7, the angle of the centreline A, as it is known from geometry, corresponds to the angle of the tangent to the centreline A at a given point, as measured in the sectional view illustrated in the figures themselves. Of course in these cases the angle can vary along the length of the centreline A. It is within the scope of the present invention that the centreline A forms an angle of less than 90 degrees along at least a portion of its length, but it is preferred that substantially the whole centreline A, or at least most of it, forms a constant angle of less than 90 degrees with the plane P, as illustrated in FIGS. 3, 4, and 5, or that alternatively the angle changes continuously along the whole length of the centreline A, as illustrated for example in FIG. 6 (curved open capillary).

It is of course possible to allow the capillaries to take the shape of a funnel such that the second opening 58 is (substantially) smaller than the first opening 57 when considering the opening size in a plain perpendicular to the centreline A. Such an embodiment is shown in FIG. 4 and FIG. 3. In FIG. 3 it is also shown that the wall 56 of the capillary may not end in the second opening 58 such that the opening forms a surface perpendicular to the centreline A but such that the wall on the portion of the capillary further apart from the wearer facing surface of the film 55 extends over the opening to further aid the film in reducing the probability of liquid migrating through the capillaries from the absorbent core on the wearer facing side of the film 55 to the garment facing side of the film (and cause leakage).

In FIG. 6 another embodiment of the capillaries useful for the present invention is shown which is curved along its length towards the wearer facing surface of the film 55. This has a similar effect as the extension of the wall 56 as shown in FIG. 3.

In FIG. 7 another preferred embodiment of a capillary according to the present invention is shown which has a first portion 257 and a second portion 258. The first portion 257 of the capillary is different in direction than the second portion 258 of the capillary 54. This difference can also be in shape, size, and form of the portions of the capillary in order to achieve the desired level of breathability while preventing liquid passage through the film in a direction from the wearer facing side towards the garment facing side.

In the preferred embodiments of the present invention comprising the resilient, three dimensional polymeric web as the polymeric film backsheet 55 with slanted capillaries it is believed that said capillaries allow air and water vapour permeability which is not hindered by them being slanted at an angle or by the shape as indicated above. At the same time the slanting and shaping according to the present invention further help the capillaries having the preferred ratio between length L and dimension D of the first opening 57 to close under pressure exerted from the wearer facing side on them such that liquid transport through the capillaries towards the outside of the article becomes nearly impossible. Hence these three-dimensional formed film layers are highly preferable in the context of breathable absorbent articles.

A further advantage related to a resilient, three dimensional polymeric web having slanted open capillaries and being comprised in a backsheet of a disposable absorbent article is the fact that such a three dimensional film does not allow a direct passage through its thickness, i.e., along a direction perpendicular to the overall film surface. Therefore this prevents portions of a further layer or of a material adjacent or applied to one surface of the polymeric three dimensional film with slanted capillaries from getting direct access to the opposite surface through the thickness of the film, i.e., through the slanted open capillaries. This is particularly useful in the context of a breathable backsheet. The slanted open capillaries in fact prevent that a bridge can be created between the two surfaces of the polymeric three dimensional film, e.g. by allowing fibres of an adjacent fibrous layer to penetrate into the capillary apertures and get in contact with a further layer adjacent to the opposite surface, so creating a preferred passage for the fluid. Further, when adhesive is used to join a polymeric three dimensional film to an adjacent layer, the slanted geometry of the open capillaries does not allow that part of the adhesive can penetrate through the open capillaries and emerge on the opposite surface, possibly contacting another layer and again creating a bridge trough the three dimensional film.

Preferred shape and size of the open capillaries 54" in a resilient, three dimensional polymeric web preferably constituting the three dimensional polymeric film 55 comprised in a preferably breathable backsheet structure of an absorbent article, according to the preferred embodiment of the present invention described so far, can be determined by the skilled man taking into account the final use of the polymeric web, for example in order to allow a good water vapour permeability, preferably also air permeability, to the backsheet structure preferably comprising such a web.

Preferably, the open capillaries 54' have a first opening 57 with a dimension D generically comprised between 0.2 mm and 5 mm, wherein D comprises the smallest dimension $D_{min}$, the average dimension $D_{av}$, and the largest dimension $D_{max}$, as defined herein. When the first opening 57 has a circular shape, dimensions $D_{min}$, $D_{av}$, and $D_{max}$ coincide, and correspond to said dimension D. They are preferably comprised between 0.4 mm and 2 mm, more preferably between 0.7 mm and 1.5 mm. If, as it is preferred, the first opening 57 has a substantially elliptical shape, with a $D_{min}$ and a $D_{max}$, corresponding to the two axes of the ellipse, both $D_{min}$ and $D_{max}$ are also more preferably comprised between 0.7 mm and 1.5 mm.

Preferably, the closed capillaries 54' have a first opening 57 with the same shape and size of that of the open capillaries 54", since this can be simpler to achieve with known processes used to manufacture the three dimensional polymeric film 55 of the present invention, preferably comprised in an absorbent article.

The length L of the open capillaries 54", as defined above, and the apparent thickness T of the three dimensional polymeric film 55, which is related to the length L, can be determined as a function of the size of the first opening 57. It is particularly preferred that the length L of the open capillaries 54" satisfies the preferred L/D ratio described above.

In a preferred example according to the present invention the resilient, three dimensional polymeric web is preferably comprised in a backsheet structure as the three-dimensional polymeric backsheet film 55 with slanted capillaries 54, and is similar to that illustrated in FIG. 8, but, differently from what is actually shown in FIG. 8, the resilient, three dimensional polymeric web further features the open capillaries 54" with the preferred L/D ratio.

The open capillaries 54" have a funnel shape substantially corresponding to that illustrated in FIG. 4, with the centreline A forming an angle of about 35 degrees with the plane P of the film, wherein $D_{min}$ is 0.9 mm, $D_{max}$ is 1.1 mm, and L is 1.9 mm. The apparent thickness T of the three dimensional polymeric film is 1.4 mm.

The closed capillaries 54' have the first opening with the same shape and size of the first opening of the closed capillaries, and have an height H of 0.5 mm. The closed capillaries constitute the 65% of the total number of capillaries of the three dimensional polymeric film 55, and are uniformly distributed among the open capillaries.

According to an alternative preferred embodiment of the present invention a preferably breathable backsheet 50 which is a dual or multiple layer composite can also be used in the absorbent article. Suitable breathable backsheets for use herein can therefore comprise a first layer such as the polymeric backsheet film 55 as described above and a second layer with said first layer being an air permeable layer. Preferred composite breathable backsheets are those having a high vapour exchange, most preferably both a high vapour and high air exchange.

As illustrated in FIG. 8, the first layer is a polymeric backsheet film 55 similar to that already described with reference to FIG. 1, but with capillaries 54 which are slanted, both the open capillaries 54" and the closed capillaries 54', even though this specific shape of the closed capillaries 54' is not particularly preferred, but can be dictated by process reasons. A symmetric shape for the closed capillaries 54' may in fact be preferable since it can provide a better resistance to deformation. It has to be noted that the polymeric backsheet film 55 of FIG. 8 does not actually show the preferred L/D ratio described hereinbefore. The polymeric backsheet film 55 is positioned between the garment facing surface of the absorbent core 40, 42, 44 and the wearer facing surface of the second layer which is indicated as layer 52 in FIG. 8. It is oriented such that it retards or prevents liquid from passing from the absorbent core 40, 42, 44 towards the outside while allowing free air flow through it.

The second layer 52 needs to provide at least water vapour permeability so as to support breathability of the article. It is not required but desirable that it also supports air permeability in order to further improve the comfort benefit from the breathability of the article. In this context suitable water vapour and air permeable layers include two-dimensional micro- or macro-apertured films, which can also be micro- or macroscopically expended films, formed apertured films and monolithic films, as well as nonwovens, or wovens.

Suitable two dimensional planar layers of the backsheet may be made of any material known in the art, but are preferably manufactured from commonly available polymeric materials. Suitable materials are for example Goretex (TM) or Sympatex (TM) type materials well known in the art for their application in so-called breathable clothing. Other suitable materials include XMP-1001 of Minnesota Mining and Manufacturing Company, St. Paul, Minn., USA and Exxaire XBF-101W, supplied by the Exxon Chemical Company. As used herein the term two dimensional planar layer refers to layers having a depth of less than 1 mm, preferably less than 0.5 mm, wherein the apertures do not protrude out of the plane of the layer. The apertured materials for use as a backsheet in the present invention may be produced using any of the methods known in the art such as described in EP 293482 and the references therein. In addition the dimensions of the apertures produced by this method may be increased by applying a force across the plane of the backsheet layer (i.e. stretching the layer).

Suitable apertured formed films include films which have discrete apertures which extend beyond the horizontal plane of the garment facing surface of the layer towards the core thereby forming protuberances. The protuberances have an orifice located at its terminating end. Preferably said protuberances are of a funnel shape, similar to those described in U.S. Pat. No. 3,929,135. The apertures located within the plane and the orifices located at the terminating end of protuberance themselves maybe circular or non circular provided the cross sectional dimension or area of the orifice at the termination of the protuberance is smaller than the cross sectional dimension or area of the aperture located within the garment facing surface of the layer. Preferably said apertured preformed films have a directional liquid transport and are positioned such that they support the prevention of liquid loss (leakage) through the backsheet. Suitable macroscopically expanded films for use herein include films as described for example in U.S. Pat. No. 4,637,819 and U.S. Pat. No. 4,591,523.

Suitable monolithic films include Hytrel (TM), available from DuPont Corporation, USA, and other such materials as described in Index 93 Congress, Session 7A "Adding value to Nonwovens", J-C. Cardinal and Y. Trouilhet, DuPont de Nemours international S.A, Switzerland. Suitable nonwovens and/or wovens are any of those well known in the art. Non-wovens such as spunbonded, melt blown or carded which are thermobonded airlayed, drylayed or even wetlaid with or without binder can be used. Particularly preferred non-wovens are multilayer non-wovens such as a composite of fine melt blown fibers with more coarse spunbonded fibers with the meltblown fibers forming the wearer facing surface of the non-woven layer.

Absorbent Article Construction

A further aspect of the present invention relates to the joining of the elements, e.g. topsheet, backsheet and absorbent core, to provide the article comprising the resilient, three dimensional polymeric web of the present invention, e.g. the disposable absorbent article described so far, when the resilient, three dimensional polymeric web of the present invention is actually comprised in an article, rather than being used as such. According to the present invention at least two, preferably all of the elements of the article are joined.

Each of said elements comprising at least one layer has a wearer facing surface and a garment facing surface. Typically, adjacent garment facing surfaces form a common interface with the wearer facing surface of an adjacent element or layer. The elements or layers are joined together across this common interface. In this manner the topsheet is joined to the absorbent core, and the core is joined to the backsheet. Furthermore, each of said topsheet, backsheet and core elements may comprise more than one layer and these layers may also be similarly joined. In addition the topsheet may be directly or indirectly joined to the backsheet at the periphery of the absorbent article to contain the absorbent core.

The elements and layers thereof may be joined by any means known in the art for affixing two adjacent layers of material, such that the layers are directly attached to one another or directly attached to one another via the joining means. Suitable joining means include adhesive, fusion bonding, ultra sonic bonding, stitching, heat (e.g. thermobonding by welding fibers at intersections or melting a polymer to attach fibers or films to each other), embossing, crimping, pressure bonds, dynamic mechanical bonds or combinations thereof. According to an embodiment of the present invention the preferred means of joining is adhesive. Suitable adhesives include non pressure sensitive and cold adhesives. The adhesive may be applied by any means known in the art such as spiral application, slot coating, spraying, spiral spraying, curtain coating, contact coating and printing, provided that the adhesive does not substantially affect the breathability, in the preferred embodiment of the present invention of a breathable absorbent article, and other functions of the elements of the article.

One means of achieving this is to use particular adhesive application methods such as open adhesive application techniques, whereby areas of the common interface are adhesive free, whilst retaining the required level of attachment/joining of the two adjacent layers or elements. In particular spiral spraying is preferred.

In a preferred embodiment of the present invention wherein the absorbent article finds utility as a sanitary napkin or panty liner, the absorbent article is also provided with a panty fastening means which provides means to attach the article to an undergarment. For example the panty fastening means may comprise a mechanical fastener such as hook and loop fasteners such as marketed under the tradename VELCRO, snaps or holders. Alternatively, the article is fastened to the undergarment by means of panty fastening adhesive on the backsheet. The panty fastening adhesive provides a means for securing the article to the panty and preferably a means for securing the article when soiled, to the fold and wrap package for convenient disposal. Typically, at least a portion of the garment facing surface of the backsheet is coated with adhesive to form the panty fastening adhesive. Any adhesive or glue used in the art for such purposes can be used for the panty fastening adhesive herein. Pressure sensitive adhesives are most preferred. Suitable adhesives include Century A-305-IV manufactured by the Century Adhesives Corporation of Columbus, Ohio, and Instant LOK 34-2823 manufactured by the National Starch and Chemical Company of Bridgewater, N.J., 3 Sigma 3153 manufactured by 3 Sigma and Fuller H-2238ZP manufactured by the H.B. Fuller Co.

In order to reduce the adverse effect on breathability of the backsheet (and thus of the article as a whole) in preferred breathable absorbent articles, the adhesive is preferably applied such that at least 60%, preferably from at least 80%, most preferably at least 90% of the surface of the backsheet is adhesive free. The required adhesiveness can still be achieved even when using reduced surface coverage by using a particular distribution such as thinner strips, discontinuous strips of adhesive, intermittent dots, random patterns or spirals.

The panty fastening adhesive is typically covered with a removable release paper or film in order to prevent the adhesive from drying out or adhering to another surface other than the panty prior to use. Any commercially available release paper or film may be used. Suitable examples include BL 30MG-A SILOX EI/O and BL 30 MG-A SILOX 4 P/O available from Akrosil Corporation.

According to the present invention the resilient, three dimensional polymeric webs can be used beneficially in the context of sanitary napkins, panty liners, incontinence articles, sweat pads and diapers, and also of protective articles such as gowns, face masks and bandages. However, sanitary napkins are particularly susceptible to the present invention. The disposable article may thus also have all those features and parts which are typical for products in the context of their intended use.

What is claimed is:

1. A resilient, three dimensional, perforated plastic web, said web consisting of a liquid impervious polymeric film (55) having a first surface, a second surface, and capillaries (54), said capillaries (54) having side walls (56) which extend away from said second surface of said backsheet film (55), said capillaries (54) having a first end (60) comprising a first opening (57) in said first surface of said film (55), and a second end (62) spaced apart from said second surface of said backsheet film (55), each of said capillaries (54) defining a conduit (70), said conduit constituted by said first end (60), said second end (62), and said side walls (56), said web being characterised in that at least 50% of said capillaries (54) are closed capillaries (54') which are closed at said second end (62), and at least 5% of said capillaries (54) are open capillaries (54") which comprise a second opening (58) at said second end (62).

2. A resilient, three dimensional, perforated plastic web according to claim 1, characterized in that said open capillaries (54") extend away from said second surface of said film (55) further than said closed capillaries (54').

3. A resilient, three dimensional, perforated plastic web according to claim 1, characterized in that from 50% to 80% of said capillaries (54) are closed capillaries (54').

4. A resilient, three dimensional perforated plastic web according to claim 1, wherein said liquid impervious polymeric film comprises an apparent thickness T defined as the distance between a first plane comprising said first ends (60) of said capillaries (54') and a second plane parallel to said first plane;

said second plane comprising points of the second ends (62)which are furthest from the first plane;

said closed capillaries (54') have a height H defined as the distance between said first plane and a third plane parallel to said first plane;

said third plane comprising the points of said second ends of said closed capillaries (54') which are furthest from said first plane;

wherein said height H of said closed capillaries (54') is less than 50% of said apparent thickness T of said liquid pervious film (55).

5. A resilient, three dimensional, perforated plastic web according to claim 1, wherein said capillaries (54) comprise a centerline A, wherein at least some of said capillaries (54) form cylinders having sectional areas which are constant in a direction extending away from said second surface when comparing areas perpendicular to said centerline A.

6. A resilient, three dimensional, perforated plastic web according to any preceding claim, characterised in that said closed capillaries (54') are all substantially identical, and said open capillaries (54") are all substantially identical respectively, wherein preferably said open and closed capillaries (54', 54") are homogeneously distributed across said backsheet film (55).

7. A resilient, three dimensional, perforated plastic web according to claim 1, characterized in that said open capillaries (54") have a length L measured along said centreline A between said first opening (57) and said second opening (58), and a largest dimension D of said first opening (57), wherein the ratio between said length L and said largest dimension D is larger than 2.

8. A resilient, three dimensional, perforated plastic web according to claim 1, characterized in that said open capillaries (54") extend away of said second surface of said film (55) at an angle (59) of less than 90° measured from said first plane of said film (55).

9. A resilient, three dimensional, perforated plastic web according to claim 1, characterized in that said resilient, three dimensional, perforated plastic web is comprised in a breathable backsheet (50) of a breathable disposable absorbent article.

10. A disposable absorbent article having a garment facing surface, which is oriented to face in the direction of a garment (21) during use of the article, and a wearer facing surface, which is oriented to face in the direction of the wearer (20) during use of the article, said article comprising at least a liquid pervious topsheet (30);

a backsheet (50);

an absorbent core (40, 42, 44) comprised between said topsheet (30) and said backsheet (50);

said backsheet (50) comprising a resilient, three dimensional web, said web consisting of a liquid impervious polymeric backsheet film (55) having a garment facing surface, a wearer facing surface, and capillaries (54), said capillaries (54) having side walls (56) which extend away from said wearer facing surface of said backsheet film (55) towards said absorbent core (40, 42, 44), said capillaries (54) having a first end (60) comprising a first opening (57) in said garment facing surface of said backsheet film (55), and a second end (62) spaced apart from said wearer facing surface of said backsheet film (55), each of said capillaries (54) defining a conduit (70), said conduit constituted by said first end (60), said second end (62), and said side walls (56), said article being characterised in that at least 50% of said capillaries (54) are closed capillaries (54') which are closed at said second end (62), and at least 5% of said capillaries (54) are open capillaries (54") which comprise a second opening (58) at said second end (62).

11. A disposable absorbent article according to claim 10, characterized in that said disposable absorbent article is breathable, wherein said backsheet (50) is also breathable.

* * * * *